US011407822B2

(12) United States Patent
Hatsell et al.

(10) Patent No.: US 11,407,822 B2
(45) Date of Patent: Aug. 9, 2022

(54) TREATMENT OF FIBRODYSPLASIA OSSIFICANS PROGRESSIVA

(71) Applicant: REGENERON PHARMACEUTICALS, INC., Tarrytown, NY (US)

(72) Inventors: Sarah J. Hatsell, Nyack, NY (US); Aris N. Economides, Tarrytown, NY (US); Vincent J. Idone, Ridgefield, CT (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/579,126

(22) Filed: Sep. 23, 2019

(65) Prior Publication Data

US 2020/0115440 A1 Apr. 16, 2020

Related U.S. Application Data

(63) Continuation of application No. 15/688,740, filed on Aug. 28, 2017, now abandoned, which is a continuation of application No. 14/850,844, filed on Sep. 10, 2015, now abandoned.

(60) Provisional application No. 62/049,869, filed on Sep. 12, 2014, provisional application No. 62/141,775, filed on Apr. 1, 2015.

(51) Int. Cl.
| | |
|---|---|
| *A61K 39/395* | (2006.01) |
| *C07K 16/22* | (2006.01) |
| *C07K 16/18* | (2006.01) |
| *A61K 38/17* | (2006.01) |
| *C07K 16/28* | (2006.01) |
| *C07K 14/705* | (2006.01) |
| *A61K 39/00* | (2006.01) |

(52) U.S. Cl.
CPC .......... *C07K 16/18* (2013.01); *A61K 38/179* (2013.01); *A61K 39/3955* (2013.01); *A61K 39/39533* (2013.01); *C07K 14/705* (2013.01); *C07K 16/22* (2013.01); *C07K 16/28* (2013.01); *C07K 16/2863* (2013.01); *A61K 2039/505* (2013.01); *C07K 2317/21* (2013.01); *C07K 2317/24* (2013.01); *C07K 2317/33* (2013.01); *C07K 2319/30* (2013.01)

(58) Field of Classification Search
CPC .. A61K 39/395; A61K 39/3955; C07K 16/18; C07K 16/22
See application file for complete search history.

(56) References Cited

U.S. PATENT DOCUMENTS

| | | | |
|---|---|---|---|
| 7,709,605 B2 | 5/2010 | Knopf et al. | |
| 7,842,663 B2 | 11/2010 | Knopf et al. | |
| 7,960,343 B2 | 6/2011 | Knopf et al. | |
| 8,128,933 B2 | 3/2012 | Knopf et al. | |
| 8,309,082 B2 * | 11/2012 | Han | A61P 1/00 424/130.1 |
| 8,486,403 B2 | 7/2013 | Knopf et al. | |
| 2013/0041017 A1 | 2/2013 | Kaplan et al. | |
| 2013/0122007 A1 | 5/2013 | Stitt et al. | |
| 2015/0037339 A1 * | 2/2015 | Gromada | A61P 21/00 424/136.1 |
| 2016/0237154 A1 | 8/2016 | Gray et al. | |
| 2016/0319009 A1 | 11/2016 | Hatsell et al. | |
| 2017/0211070 A1 | 7/2017 | Hino et al. | |
| 2018/0111983 A1 | 4/2018 | Hatsell et al. | |
| 2019/0153085 A1 | 5/2019 | Hatsell et al. | |
| 2021/0061898 A1 | 3/2021 | Hatsell et al. | |

FOREIGN PATENT DOCUMENTS

| | | | |
|---|---|---|---|
| WO | WO 2008-097541 A2 | 8/2008 | |
| WO | WO 2009-114180 A1 | 9/2009 | |
| WO | WO 2009-137075 A1 | 11/2009 | |
| WO | WO 2013-063536 A1 | 5/2013 | |
| WO | WO 2014-051109 A1 | 4/2014 | |
| WO | WO 2015-152183 A1 | 10/2015 | |
| WO | WO-2015152183 A1 * | 10/2015 | ........... C07K 14/473 |
| WO | WO 2016-039796 A2 | 3/2016 | |
| WO | WO 2016-176341 A1 | 11/2016 | |

OTHER PUBLICATIONS

Knappik et al., J. Mol. Biol., 2000, vol. 296(1):57-86.*
Nair et al., J. Immunol., 2002, vol. 168(5):2371-2382.*
Lu et al., J. Immunol., 2004, vol. 173(6):3972-3978.*
EP 19177741.6 Extended European Search Report dated Dec. 19, 2019.
U.S. Appl. No. 16/195,679 Non-Final Office Action dated Mar. 12, 2020.
Lach-Trifilieff, et al., "An Antibody Blocking Activin type II Receptors Induces Strong Skeletal Muscle Hypertrophy and Protects from Atrophy," Mol. Cell. Biol., Published online ahead of print on Dec. 2, 2013 doi:10.1128/MCB.01307-13.
Invitation to Pay Additional Fees for PCT/US2015/000100, dated Jan. 14, 2016.
Mohedas, et al., "Development of an ALK2-Based BMP Type I Receptor Kinase Inhibitor," ACS Chemical Biology, 8(6): 1291-1302, (Apr. 2, 2013).

(Continued)

*Primary Examiner* — Xiaozhen Xie
(74) *Attorney, Agent, or Firm* — Alston & Bird LLP; Christopher Westberg

(57) ABSTRACT

Methods for treating Fibrodysplasia Ossificans Progressiva (FOP) are provided. Such methods involve administering to a subject having FOP an effective regime of an activin receptor type 2A (ACVR2A) and/or an activin receptor type 2B (ACVR2B) antagonist or an activin receptor type 1 (ACVR1) antagonist. Antagonists include fusion proteins of one or more extracellular domains (ECDs) of ACVR2A, ACVR2B and/or ACVR1 and the Fc domain of an immunoglobulin heavy chain, and antibodies against ACVR2A, ACVR2B, ACVR1 or Activin A.

6 Claims, 5 Drawing Sheets

Specification includes a Sequence Listing.

(56) References Cited

OTHER PUBLICATIONS

Kaplan, et al., "From Mysteries to medicines: drug development for fibrodysplasia ossificans progressiva, Expert Opinion on Orphan Drugs," 1:8, 637-649, Published online Jul. 25, 2013.
Bagarova, et al., "Constitutively active ALK2 receptor mutants require Type II receptor cooperation," Molecular and Cellular Biology, 33(12): 2413-2424, Jun. 15, 2013.
Lotinun, et al., "A soluble activin receptor Type IIA fusion protein (ACE-011) increases bone mass via a dual anabolic-antiresorptive effect in Cynomolgus monkeys," Bone, 46(4): 1082-1088, Apr. 1, 2010.
Haupt, et al., "ACVR1 p.Q207E causes classic fibrodysplasia ossificans progressiva and is functionally distinct from the engineered constitutively active ACVR1 p.Q207D variant," Human Molecular Genetics, 23(20): 5364-5377, May 22, 2014.
Hatsell, et al., "ACVR1R206H receptor mutation causes fibrodysplasia ossificans progressiva by imparting responsiveness to activin A," Science Translational Medicine, 7(303): 303ra137-303ra137, Sep. 2, 2015.
International Search Report and Written Opinion of the International Searching Authority for PCT/US2015/000100 dated May 3, 2016.
International Search Report and Written Opinion of the International Searching Authority for PCT/US2016/029585 dated Jun. 9, 2016.
Songting, et al., "Antisense-Oligonucleotide Mediated Exon Skipping in Activin-Receptor-Like Kinase 2: Inhibiting the Receptor That Is Overactive in Fibrodysplasia Ossificans Progressiva," PLOS ONE, 8(7): e69096, Jul. 4, 2013.
Yu, et al., "BMP type 1 receptor inhibition reduces heterotopic ossification," Nature Medicine, 14(12): 1363-1369, Dec. 1, 2008.
"New: 505420 BMP Inhibitor III, LDN-212584—Calbiochem," EMD Millipore Flyer, May 27, 2014.
Carrancio, et al., "An activin receptor IIA ligand trap promotes erythropoiesis resulting in a rapid induction of red blood cells and hemoglobin," British Journal of Hematology, 165(6) :870-882 (2014).
McPherron, et al., "Soluble activin receptor type IIB treatment does not cause fat loss in mice with diet-induced obesity," Diabetes Obes Metab., 14(3): 279-282, Mar. 2012.
Sako, et al., "Characterization of the Ligand Binding Functionality of the Extracellular Domain of Activin Receptor Type IIB," Journal of Biological Chemistry, 285(27): 21037-21048, Jul. 2, 2010.
Pearsall, et al., "A soluble activiin type IIA receptor induces bone formation and improves skeletal integrity," PNAS, 105(19): 7082-7087, May 13, 2008.
Sieber, et al., "Recent advances in BMP receptor signaling," Cytokine & Growth Factor Reviews, 20(2009): 343-355, Nov. 7, 2009.
U.S. Appl. No. 14/850,844, Requirement for Restriction/Election dated Sep. 12, 2006.
U.S. Appl. No. 14/850,844, Non-final Office Action dated Feb. 28, 2017.
U.S. Appl. No. 15/140,411, Requirement for Restriction/Election dated Sep. 25, 2017.
PCT/US2015/000100 International Preliminary Report on Patentability dated Mar. 14, 2017.
PCT/US2016/029585 International Preliminary Report on Patentability dated Oct. 31, 2017.
U.S. Appl. No. 15/140,411, Non-Final Office Action dated May 18, 2018.
U.S. Appl. No. 15/688,740, Requirement for Restriction/Election dated Jun. 18, 2018.
U.S. Appl. No. 15/688,740, Non-Final Office Action dated Mar. 22, 2019.
Knappik, et al., "Fully Synthetic Human Combinatorial Antibody Libraries (HuCAL) Based on Modular Consensus Frameworks and CDRs Randomized with Trinucleotides," J. Mol. Biol., 296, pp. 57-86, (2000).
Nair, et al., "Epitope Recognition by Diverse Antibodies Suggests Conformational Convergence in an Antibody Response," The Journal of Immunology, 168: pp. 2371-2382, (2002).
Lu, et al., "The Binding Sites for Competitive Antagonistic, Allosteric Antagonistic, and Agonistic Antibodies to the I Domain of Integrin LFA-1[1]," The Journal of Immunology, 173: pp. 3972-3978, (2004).
US 16/195, 679 Restriction Requirement dated Nov. 5, 2019.

\* cited by examiner

SEQUENCE LISTING

<160> NUMBER OF SEQ ID NOS: 24

<210> SEQ ID NO 1
<211> LENGTH: 126
<212> TYPE: PRT
<213> ORGANISM: Artificial Sequence
<220> FEATURE:
<223> OTHER INFORMATION: Synthesized

<400> SEQUENCE: 1

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser
        115                 120                 125
```

<210> SEQ ID NO 2
<211> LENGTH: 8
<212> TYPE: PRT
<213> ORGANISM: Artificial Sequence
<220> FEATURE:
<223> OTHER INFORMATION: Synthesized

<400> SEQUENCE: 2

```
Gly Gly Ser Phe Ser Ser His Phe
 1               5
```

<210> SEQ ID NO 3
<211> LENGTH: 7
<212> TYPE: PRT
<213> ORGANISM: Artificial Sequence
<220> FEATURE:
<223> OTHER INFORMATION: Synthesized

<400> SEQUENCE: 3

Ile Leu Tyr Thr Gly Gly Thr
1               5

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

Ala Arg Ala Arg Ser Gly Ile Thr Phe Thr Gly Ile Ile Val Pro Gly
1               5                   10                  15

Ser Phe Asp Ile
            20

<210> SEQ ID NO 5
<211> LENGTH: 108
<212> TYPE: PRT
<213> ORGANISM: Artificial Sequence
<220> FEATURE:
<223> OTHER INFORMATION: Synthesized

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 6
<211> LENGTH: 7
<212> TYPE: PRT
<213> ORGANISM: Artificial Sequence
<220> FEATURE:
<223> OTHER INFORMATION: Synthesized

<400> SEQUENCE: 6

Gln Ser Val Ser Ser Ser Tyr
1               5

<210> SEQ ID NO 7
<211> LENGTH: 3
<212> TYPE: PRT
<213> ORGANISM: Artificial Sequence
<220> FEATURE:

```
<223> OTHER INFORMATION: Synthesized

<400> SEQUENCE: 7

Gly Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Gln Gln Tyr Gly Ser Ser Pro Trp Thr
1               5

<210> SEQ ID NO 9
<211> LENGTH: 125
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Arg
1               5                   10                  15

Ser Leu Arg Leu Ser Cys Lys Ala Ser Gly Phe Ala Phe Asp Asp Phe
            20                  25                  30

Ala Met His Trp Val Arg Gln Ala Pro Gly Lys Gly Leu Glu Trp Val
        35                  40                  45

Ser Gly Ile Val Trp Asn Ser Gly Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Thr Glu Asp Thr Ala Leu Tyr Phe Cys
                85                  90                  95

Val Lys Asp Met Val Arg Gly Leu Met Gly Phe Asn Tyr Tyr Gly Met
            100                 105                 110

Asp Val Trp Gly Gln Gly Thr Thr Val Thr Val Ser Ser
        115                 120                 125

<210> SEQ ID NO 10
<211> LENGTH: 8
<212> TYPE: PRT
<213> ORGANISM: Artificial Sequence
<220> FEATURE:
<223> OTHER INFORMATION: Synthesized

<400> SEQUENCE: 10

Gly Phe Ala Phe Asp Asp Phe Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized

<400> SEQUENCE: 11

Ile Val Trp Asn Ser Gly Asp Ile
1               5
```

<210> SEQ ID NO 12
<211> LENGTH: 18
<212> TYPE: PRT
<213> ORGANISM: Artificial Sequence
<220> FEATURE:
<223> OTHER INFORMATION: Synthesized

<400> SEQUENCE: 12

```
Val Lys Asp Met Val Arg Gly Leu Met Gly Phe Asn Tyr Tyr Gly Met
1               5                   10                  15

Asp Val
```

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Thr Tyr
            20                  25                  30

Leu Val Trp Tyr Arg Gln Arg Pro Gly Gln Ala Pro Ser Leu Leu Ile
        35                  40                  45

Tyr Asp Ala Ser Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

<210> SEQ ID NO 14
<211> LENGTH: 6
<212> TYPE: PRT
<213> ORGANISM: Artificial Sequence
<220> FEATURE:
<223> OTHER INFORMATION: Synthesized

<400> SEQUENCE: 14

```
Gln Thr Ile Ser Thr Tyr
1               5
```

<210> SEQ ID NO 15
<211> LENGTH: 3
<212> TYPE: PRT
<213> ORGANISM: Artificial Sequence
<220> FEATURE:
<223> OTHER INFORMATION: Synthesized

<400> SEQUENCE: 15

```
Asp Ala Ser
1
```

<210> SEQ ID NO 16
<211> LENGTH: 9
<212> TYPE: PRT
<213> ORGANISM: Artificial Sequence
<220> FEATURE:

<223> OTHER INFORMATION: Synthesized

<400> SEQUENCE: 16

Gln Gln Arg Ser Asn Trp Pro Ile Thr
1               5

<210> SEQ ID NO 17
<211> LENGTH: 106
<212> TYPE: PRT
<213> ORGANISM: Homo sapiens

<400> SEQUENCE: 17

Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 18
<211> LENGTH: 122
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Phe Cys
                85                  90                  95

Ala Arg Asp Arg Asp Tyr Gly Val Asn Tyr Ala Phe Asp Ile Trp
            100                 105                 110

Gly Gln Gly Thr Met Val Thr Val Ser Ser
        115                 120

<210> SEQ ID NO 19
<211> LENGTH: 11
<212> TYPE: PRT
<213> ORGANISM: Homo sapiens

<400> SEQUENCE: 19

Ser Gly Asp Lys Leu Gly Asp Lys Tyr Ala Cys
1               5                   10

```
<210> SEQ ID NO 20
<211> LENGTH: 7
<212> TYPE: PRT
<213> ORGANISM: Homo sapiens

<400> SEQUENCE: 20

Gln Asp Ser Lys Arg Pro Ser
1               5

<210> SEQ ID NO 21
<211> LENGTH: 9
<212> TYPE: PRT
<213> ORGANISM: Homo sapiens

<400> SEQUENCE: 21

Gln Ala Trp Asp Ser Ser Thr Ala Val
1               5

<210> SEQ ID NO 22
<211> LENGTH: 10
<212> TYPE: PRT
<213> ORGANISM: Homo sapiens

<400> SEQUENCE: 22

Gly Tyr Thr Phe Thr Ser Tyr Gly Leu Ser
1               5                   10

<210> SEQ ID NO 23
<211> LENGTH: 17
<212> TYPE: PRT
<213> ORGANISM: Homo sapiens

<400> SEQUENCE: 23

Trp Ile Ile Pro Tyr Asn Gly Asn Thr Asn Ser Ala Gln Lys Leu Gln
1               5                   10                  15
Gly

<210> SEQ ID NO 24
<211> LENGTH: 13
<212> TYPE: PRT
<213> ORGANISM: Homo sapiens

<400> SEQUENCE: 24

Asp Arg Asp Tyr Gly Val Asn Tyr Asp Ala Phe Asp Ile
1               5                   10
```

TREATMENT OF FIBRODYSPLASIA OSSIFICANS PROGRESSIVA

CROSS REFERENCE TO RELATED APPLICATION

This application is a continuation of U.S. application Ser. No. 15/688,740 filed Aug. 28, 2017, now abandoned, which is a continuation of U.S. application Ser. No. 14/850,844 filed Sep. 10, 2015, now abandoned, which claims the benefit under 35 USC 119§ of U.S. provisional Application Nos. 62/049,869 filed Sep. 12, 2014, and 62/141,775 filed Apr. 1, 2015, the disclosures of each of which are herein incorporated by reference in their entireties.

REFERENCE TO A SEQUENCE LISTING

The application refers to sequences written in the file 503606_SEQLST.TXT, created on, Sep. 20, 2019, which is 10,051 bytes. The information contained in this file is hereby incorporated by reference.

BACKGROUND

Fibrodysplasia Ossificans Progressiva (FOP) is an autosomal dominant disorder characterized by early onset, episodic and progressive ossification of skeletal muscle and associated connective tissue. FOP is driven by mutations in the intracellular domain of ACVR1 (ALK2), with the great majority altering Arginine 206 to Histidine (R206H) (Pignolo, R. J. et al. 2011, *Orphanet J. Rare Dis.* 6:80). ACVR1 is a type I receptor for bone morphogenic proteins (BMPs). The R206H mutation, among others, is believed to increase the sensitivity of the receptor to activation and render it more resistant to silencing. No effective medical therapy is known for FOP.

SUMMARY OF THE CLAIMED INVENTION

The invention provides methods of treating Fibrodysplasia Ossificans Progressiva (FOP), comprising administering to a subject having FOP an effective regime of an activin receptor type 2A (ACVR2A) and/or an activin receptor type 2B (ACVR2B) antagonist. In some methods, the antagonist comprises an ACVR2A or ACVR2B extracellular domain. In some methods, the antagonist comprises an ACVR2A or ACVR2B Fc fusion protein. In some methods, the isotype of the Fc fusion protein is human IgG1. In some methods, the antagonist comprises an ACVR2A extracellular domain linked to an ACVR2B extracellular domain. In some methods, the antagonist further comprises an Fc domain. In some methods, the antagonist comprises an ACVR2A extracellular domain fused to a first Fc domain and an ACVR2B extracellular domain fused to a second Fc domain wherein the first and second Fc domains are complexed with one another. In some methods, the antagonist comprises a linker between the ACVR2A and ACVR2B extracellular domains, each fused to an Fc domain. In some methods, the antagonist is a fusion protein comprising an ACVR2A extracellular domain, an ACVR2B extracellular domain and an Fc domain. In some methods, an effective regime of an ACVR2A antagonist and an ACVR2B antagonist is administered. In some methods, the ACVR2A antagonist is an ACVR2A Fc fusion protein and the ACVR2B antagonist is an ACVR2B Fc fusion protein. In some methods, the antagonist is an antibody to ACVR2A or ACVR2B. In some methods, the subject does not have and is not at risk of type II diabetes, muscular dystrophy, amyotrophic lateral sclerosis (ALS) or osteoporosis.

The invention further provides methods of treating FOP, comprising administering to a subject having FOP an effective regime of an activin receptor type 1 (ACVR1) antagonist. In some methods, the antagonist comprises an ACVR1 extracellular domain. In some methods, the antagonist comprises an ACVR1 fusion protein. In some methods, the isotype of the Fc fusion protein is human IgG1. In some methods, the antagonist is an antibody to ACVR1.

The invention further provides methods of treating Fibrodysplasia Ossificans Progressiva (FOP), comprising administering to a subject having FOP an effective regime of an activin receptor type 2A (ACVR2A) and/or an activin receptor type 2B (ACVR2B) antagonist in combination with an activin receptor type 1 (ACVR1) antagonist. In some methods, the antagonist comprises an ACVR1, ACVR2A and/or ACVR2B extracellular domain. In some methods, the antagonist comprises an ACVR1, ACVR2A and/or ACVR2B Fc fusion protein. In some methods, the isotype of the Fc fusion protein is human IgG1. In some methods, the antagonist is an antibody to ACVR1, ACVR2A and/or ACVR2B.

The invention further provides a method of treating Fibrodysplasia Ossificans Progressiva (FOP), comprising administering to a subject having FOP an effective regime of an antibody against Activin A. Optionally, the antibody competes for binding with antibody comprising the heavy and light chain variable regions of the antibody designated H4H10446P, H4H10430P or A1. Optionally, the antibody comprises the heavy and light chain variable regions of the antibody designated H4H10446P, H4H10430P or A1. Optionally, the antibody is a chimeric, veneered, humanized or human antibody. Optionally, the antibody is an intact antibody. Optionally, the antibody is a human kappa IgG1 antibody.

DEFINITIONS

Figure 1:
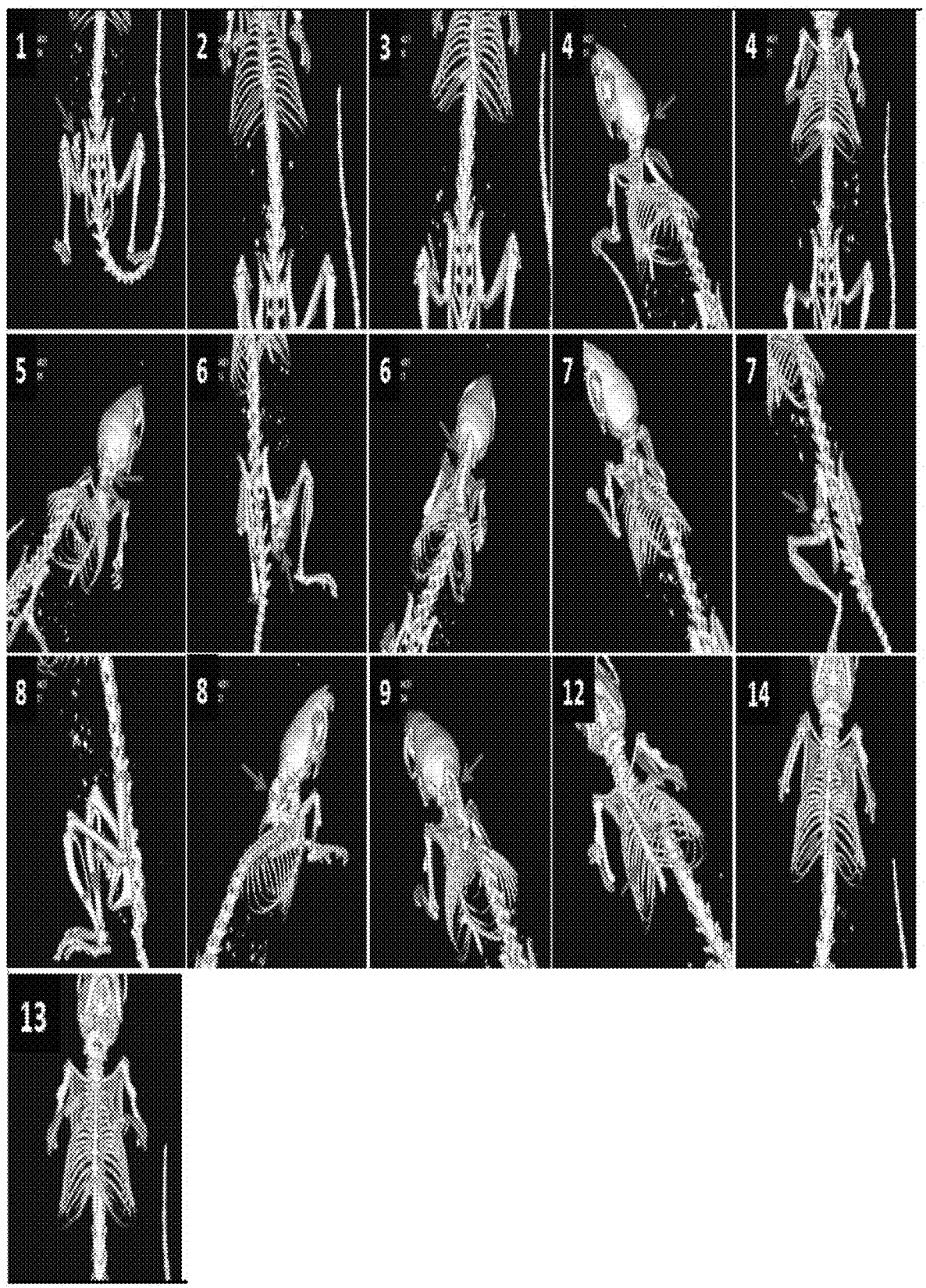
FIG. 1 shows microCT data from mice showing ectopic bone formation at 6 weeks post initiation of tamoxifen administration with and without ACVR2A-Fc/ACVR2B-Fc treatment. Nine out of ten control mFc treated mice (numbers 1 to 9) showed ectopic bone formation at 6 weeks post tamoxifen administration. Most common locations are hind limb, neck region and sternum. Two out of eleven ACVR2A-Fc/ACVR2B-Fc treated mice (numbers 12 and 14) showed ectopic bone formation at 6 weeks post tamoxifen administration. The ectopic bone lesions in these two mice were of small size compared to those seen in the mFc treated group and both located at the sternum.

Antagonists are typically provided in isolated form. This means that an antagonist is typically at least 50% w/w pure of interfering proteins and other contaminants arising from its production or purification, but does not exclude the possibility that the antagonist is combined with an excess of pharmaceutical acceptable carrier(s) or other vehicle intended to facilitate its use. Sometimes antagonists are at least 60, 70, 80, 90, 95 or 99% w/w pure of interfering proteins and contaminants from production or purification.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. For other proteins, sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements can include other elements not specifically recited. For example, a composition that comprises antibody can contain the antibody alone or in combination with other ingredients.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. Nos. 5,859,205 and 6,881,557; Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region, respectively, when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al., Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody, but replaces other variable region framework residues that can contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., Cys muoma 2:361-367 (1983); Oestberg, U.S. Pat. No. 4,634,664; and Engleman et al., U.S. Pat. No. 4,634,666. The monoclonal antibodies can also be produced by transgenic mice bearing human immune system genes, such as the VelocImmune® mouse from Regeneron Pharmaceuticals, Inc. (Murphy, PNAS 111 no.

14, 5153-5158 (2014), Xenomouse, Jakobovits, Nature Biotechnology 25, 1134-1143 (2007) or HuMAb mouse from Medarex, Inc. (Lonberg, Handbook Exp. Pharmacol. 181, 69-97 (2008); Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991). Human antibodies can also be produced by phage display methods (see, e.g., Dower et al., WO 91/17271 and McCafferty et al., WO 92/01047, U.S. Pat. Nos. 5,877,218, 5,871,907, 5,858, 657, 5,837,242, 5,733,743 and 5,565,332).

When an antagonist is said to retain a property of a parental antibody from which it was derived, the retention can be complete or partial. Complete retention of an activity means the activity of the antagonist is the same within experimental error or greater than that of the molecule from which it was derived. Partial retention of activity means activity significantly above background level of a negative control (i.e., beyond experimental error) and preferably at least 50% of the corresponding activity of the molecule from which it was derived.

Two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50%, but preferably 75%, 90% or 99%, as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

DETAILED DESCRIPTION

I. Overview

Methods for treating Fibrodysplasia Ossificans Progressiva (FOP) are provided. Such methods involve administering to a subject having FOP an effective regime of an activin receptor type 2A (ACVR2A) and/or an activin receptor type 2B (ACVR2B) antagonist and/or an activin receptor type 1 (ACVR1) antagonist, and/or an Activin A antagonist. Such antagonists include fusion proteins comprising one or more extracellular domains (ECDs) of ACVR2A, ACVR2B and/or ACVR1 and the Fc domain of an immunoglobulin heavy chain. Antibody antagonists of ACVR2A, ACVR2B, ACVR1 or Activin A are also provided.

II. ACVR1, ACVR2A, ACVR2B and Activin A

The transforming growth factor β (TGFβ) superfamily of ligands includes, for example, bone morphogenetic proteins (BMPs) and growth and differentiation factors (GDFs). The receptors for these ligands are heteromeric receptor complexes made up of type I and type II transmembrane serine/threonine kinase receptors. Examples of type I receptors include activin receptor type IA (ACTRIA, ACVR1, or ALK2), BMP receptor type IA and BMP receptor type IB. Examples of type II receptors include activin receptors type IIA and IIB (ACTRIIA or ACVR2A and ACTRIIB or ACVR2B) and BMP receptor type II. The ligands of the TGFβ superfamily each have differing affinities for the different type I and type II receptors.

Both the type I and type II receptors have an extracellular ligand binding domain (ECD) and an intracellular serine/threonine kinase domain. In addition, the type I receptors have a glycine/serine-rich region (GS-box) preceding the kinase domain and a L45 loop within the kinase domain. Both receptors work together for ligands to activate downstream signaling pathways, such as Smad and non-Smad signaling pathways. Activation involves ligand binding, ligand-receptor oligomerization and transphosphorylation of the GS box of the type I receptor by the type II receptor kinase. The type II receptor kinase is constitutively active and has a role in ligand binding and activation of the type I receptor.

ACVR1, also known as activin a receptor type I, ACVR1A, ACVRLK2, or ALK2, is a type I receptor for the TGFβ superfamily of ligands. ACVR1 has serine/threonine kinase activity and phosphorylates Smad proteins and activates downstream signaling pathways. ACVR1 is found in many tissues of the body including skeletal muscle and cartilage and helps to control the growth and development of the bones and muscles. As described elsewhere herein, certain mutations in the ACVR1 gene cause FOP. Examples of ACVR1 activity include the ability to bind to ligands, the ability to form a complex with a type II receptor, or the ability to activate downstream signaling pathways, such as the Smad pathway.

ACVR2, also known as activin receptor type II, is a type II receptor for the TGFβ superfamily of ligands. There are at least two ACVR2 receptors, for example, activin receptor type IIA (ACVR2A or ACTRIIA) and activin receptor type IIB (ACVR2B or ACTRIIB). Reference to ACVR2 includes either or both of ACVR2A and ACVR2B. ACVR2A and ACVR2B can be expressed in multiple tissues, including skeletal muscle, stomach, heart, endometrium, testes, prostate, ovary, and neural tissues.

On ligand binding, an ACVR2 receptor forms a complex with a type I receptor, such as ACVR1, and phosphorylates the GS box of the type I receptor, thus enhancing the kinase activity of the type I receptor. Examples of ACVR2A and ACVR2B activity include the ability to bind to ligands, the ability to form a complex with a type I receptor, or the ability to phosphorylate a type I receptor.

An exemplary form of human ACVR2A has Swiss Prot accession number P27037. Residues 1-19 are a signal peptide, residues 20-135 are an extracellular domain, residues 59-116 are an activin types I and II receptor domain, residues 136-161 are a transmembrane domain and residues 162-513 are a cytoplasmic domain. An exemplary form of human ACVR2B is assigned Swiss Prot Number Q13705. Residues 1-18 are a signal sequence, residues 19-137 are an extracellular domain, residues 27-117 are an activin types I and II receptor domain, residues 138-158 are a transmembrane domain and residues 159-512 are a cytoplasmic domain. An exemplary form of human ACVR1 has Swiss Prot accession number Q04771. Residues 1-20 are a signal sequence, residues 21-123 are extracellular domain, residues 33-104 are an activin types I and II receptor domain, residues 124-146 are a transmembrane domain and residues 147-509 are a cytoplasmic domain. Reference to any of ACVR1, ACVR2A and ACVR2B includes these exemplary forms, known isoforms and polymorphisms thereof, such as those listed in the Swiss Prot database, cognate forms from other species, and other variants having at least 90, 95, 96, 97, 98 or 99% sequence identity with an exemplified form.

Residues of forms of ACVR2A, ACVR2B and ACVR1 other than the exemplified sequences defined above are numbered by maximum alignment with the corresponding exemplified sequences so aligned residues are allocated the same number. Substitutions from exemplified sequences can be conservative or non-conservative substitutions. Reference to ACVR1, ACVR2A or ACVR2B also includes intact extracellular domains (e.g., residues 20-135, 19-137 or 21-123 of ACVR2A, ACVR2B and ACVR1, respectively) or a portion thereof free or substantially free of transmembrane and cytoplasmic portion. Portions of an extracellular domain retain sufficient residues of the intact extracellular domain to bind at least one ligand or counter receptor that binds to the intact extracellular domain and thereby antagonize the relevant receptor (e.g., residues 59-116, 27-117 or 33-104 of ACVR2A, ACVR2B and ACVR1, respectively).

Activin A in humans can exist as a homo or heterodimeric protein. The homodimeric protein contains a homodimeric beta A subunit pair. The heterodimeric protein contains a beta subunit and a beta B, beta C or beta E subunit (i.e., beta A beta B, beta A beta C, or beta A beta E. The subunits are each expressed as precursor polypeptides including a signal peptide, propeptide and mature polypeptide. An exemplary form of human beta A subunit precursor is a polypeptide of length 426 amino acids designated Swiss Prot P08476 of which residues 1-20 are a signal peptide, residues 21-310 are a propeptide and residues 311-426 are the mature polypeptide. An exemplary form of a beta B subunit precursor polypeptide is designated Swiss Prot P09529 of which residues 1-28 are a signal peptide, residues 29-292 a propeptide and residues 293-407 a mature polypeptide. An exemplary form of a beta C subunit is designated Swiss Prot P55103, of which residues 1-18 are a signal peptide, residues 19-236 are a propeptide and residues 237-352 are a mature polypeptide. An exemplary form of a beta E subunit precursor is designated Swiss Prot P58166 of which residues 1-19 are a signal peptide, residues 20-236 are a propeptide and residues 237-350 are a mature polypeptide. Several variants of these sequences are known as described in the Swiss Prot Data base. Reference to Activin A includes any of the beta A homodimer, beta A beta B, beta A beta C and beta A beta E heterodimer forms, as well as their subunits, as well as their precursors in which subunits are attached to the propeptide and/or signal peptide defined by the exemplary Swiss Prot sequences provided or other natural occurring human forms of these sequences. Activin A signals through binding to ACVR2A or ACVR2B, but is not known to be a ligand for ACVR1.

III. Antagonists of ACVR1, ACVR2A, ACVR2B

Antagonists of the type I receptor ACVR1 and of the type II receptor ACVR2 proteins (e.g., ACVR2A and/or ACVR2B) are provided for treating FOP. Such antagonists can antagonize receptors directly by binding to the receptor (as for an antibody to ACVR1, ACVR2A or ACVR2B) or indirectly by binding to a ligand or counter receptor and inhibiting the ligand or counter receptor from binding to ACVR1, ACVR2A or ACVR2B (as for a fusion protein of ACVR1, ACVR2A or ACVR2B) among other mechanisms. Antagonists of ACVR2A and ACVR2B can also bind to Activin A.

An ACVR1, ACVR2A or ACVR2B antagonist provided herein can inhibit or reduce the activity of ACVR1, ACVR2A and/or ACVR2B by at least 1%, 5%, 10%, 20%, 30%, 40%, 50%, 60%, 70%, 80%, 90%, 95%, 99% or more relative to a control cell or animal model that did not receive the antagonist.

Any antagonist of ACVR1, ACVR2A or ACVR2B can be used in the methods for treating FOP. The antagonist can comprise, for example, an ACVR1, ACVR2A or ACVR2B polypeptide, such as an extracellular domain, an antagonist antibody, or a small molecule inhibitor.

A. Extracellular Domains of ACVR1, ACVR2A and ACVR2B Polypeptides

Antagonists include ACVR1, ACVR2A and ACVR2B proteins and fragments thereof effective to inhibit at least one activity of ACVR1, ACVR2A and ACVR2B, respectively. Such antagonists typically include the extracellular domain of ACVR1, ACVR2A or ACVR2B or a portion thereof. Preferably, such extracellular domains are entirely or substantially free of the transmembrane and cytoplasmic regions (i.e., any remaining residues from these regions have no significant effect on function of the extracellular domain). In other words, the ACVR2A, ACVR2B or ACVR1 component of such antagonists consists of or consists essentially of the entire extracellular domain of ACVR2A, ACVR2B or ACVR1 or a portion thereof as defined above Such antagonists may or may not include other component(s) distinct from ACVR2A, ACVR2B or ACVR1 as further described below. Such extracellular domains free or substantially free of transmembrane and cytoplasmic domains are soluble. Such extracellular domains can function as an antagonist by binding to a soluble ligand or counter receptor, effectively competing with the ligand or counter receptor binding to the ACVR1, ACVR2A or ACVR2B cell surface receptor, thereby modulating (reducing) the availability of the ligand or counter receptor in vivo.

Soluble extracellular domains can be initially expressed with a signal sequence, which is cleaved in the course of expression. The signal sequence can be a native signal sequence of an ACVR1, ACVR2A or ACVR2B, such as those described in U.S. Pat. No. 7,709,605, which is incorporated by reference herein in its entirety, or can be a signal sequence from a different protein such honey bee melittin (HBM) or tissue plasminogen activator (TPA). Alternatively, soluble extracellular ACVR1, ACVR2A or ACVR2B polypeptides can be synthesized or expressed without a signal sequence.

The ECDs or ligand binding domains of ACVR1, ACVR2A and ACVR2B are highly conserved among species including mouse and human. The ECDs contain a cysteine rich region and a C-terminal tail region. The ECDs of ACVR1, ACVR2A and ACVR2B bind to a diverse group of TGFβ family ligands, including, for example, Activin A, myostatin (GDF-8), GDF-11 and BMPs. See, e.g., Souza et al. (2008) Molecular Endocrinology 22(12):2689-2702.

Examples of ACVR2A and ACVR2B polypeptides and soluble ACVR2A and ACVR2B polypeptides include those disclosed in U.S. Pat. Nos. 7,842,633; 7,960,343; and 7,709,605, each of which is incorporated by reference herein in their entirety.

The ECD of an ACVR1, ACVR2A or ACVR2B polypeptide can be mutated such that the variant polypeptide has altered ligand binding properties (e.g., binding specificity or affinity). Some variant ACVR1, ACVR2A or ACVR2B polypeptides have altered binding affinity (e.g., elevated or reduced) for a specific ligand. Variants have at least 90%, 91%, 92%, 93%, 94%, 95%, 96%, 97%, 98%, 99% sequence identity to the naturally occurring ACVR1, ACVR2A or ACVR2B sequences, and retain biological activity and hence have an ACVR1, ACVR2A or ACVR2B activity as described elsewhere herein. Active variants and fragments of ACVR2A and ACVR2B are described, for example, in U.S. Pat. Nos. 7,842,633; 7,960,343; and 7,709,605, each of which is incorporated by reference herein in its entirety.

Assays to measure ACVR1, ACVR2A or ACVR2B activity are disclosed in e.g., U.S. Pat. Nos. 7,842,633; 7,960,343; and 7,709,605. For example, an ACVR1, ACVR2A or ACVR2B polypeptide variant can be screened for the ability to bind a ligand or for the ability to prevent binding of a ligand to an ACVR1, ACVR2A or ACVR2B receptor protein.

B. Fusion Proteins

The ACVR1, ACVR2A and ACVR2B polypeptides described above can be expressed as fusion proteins having at least a portion of an ACVR1, ACVR2A and/or ACVR2B polypeptide and one or more fusion domains.

Fusion domains include an immunoglobulin heavy chain constant region (Fc), human serum albumin (HSA), glutathione S transferase (GST), protein A, protein G, or any fusion domain which can be useful in stabilizing, solubilizing, isolating or multimerizing a fusion protein.

An Fc domain of an immunoglobulin heavy chain is a preferred domain for fusion proteins. Fusions with the Fc portion of an immunoglobulin confer desirable pharmacokinetic properties on a wide range of proteins (e.g., increases stability and/or serum half-life of the protein). Thus, the invention provides fusion proteins comprising at least one ECD of an ACVR1, ACVR2A and/or ACVR2B fused to an Fc domain of an immunoglobulin.

The Fc domain for use in the present methods can be from any immunoglobulin. Any of the various classes of immunoglobulin can be used, including IgG, IgA, IgM, IgD and IgE. Within the IgG class there are different subclasses or isotypes, including, for example, $IgG_1$, $IgG_2$, $IgG_3$ and $IgG_4$. In one embodiment, the Fc fusion protein comprises the Fc domain of an IgG molecule. In a further embodiment, the Fc domain is from an $IgG_1$ molecule. The immunoglobulin molecule can be of any animal type, including, for example, a mammal, a rodent, a human, a mouse, a rat, a hamster or a rabbit. In one embodiment, the immunoglobulin Fc domain is from a mammal. In another embodiment, the Fc domain is from a human. In yet another embodiment, the Fc domain is from a rodent, such as a mouse or rat. In a specific embodiment, the Fc domain of the fusion protein is from human IgG1.

The Fc-fusion proteins provided herein can be made by any method known in the art. The Fc-fusion proteins can include at least CH2 and CH3 regions, and typically at least a portion of a hinge region. Although the CH1 region can be present, it is typically omitted in fusion proteins.

The fusion can be made at any site within the Fc portion of an immunoglobulin constant domain. Fusions can be made to the C-terminus of the Fc portion of a constant domain, or immediately N-terminal to the CH1 region of the heavy chain. Particular sites can be selected to optimize the biological activity, secretion or binding characteristics of the Fc-fusion protein.

In some cases, a nucleic acid encoding the ECD of ACVR1, ACVR2A and/or ACVR2B is fused C-terminally to a nucleic acid encoding the N-terminus of an immunoglobulin constant domain sequence. In other cases, N-terminal fusions are also possible. It is also possible to fuse an ECD of ACVR1, ACVR2A and/or ACVR2B to both the N-terminus and the C-terminus of an immunoglobulin constant domain sequence.

For the production of immunoglobulin fusions, see also U.S. Pat. Nos. 5,428,130, 5,843,725, 6,018,026 and WO2005/070966, each of which is incorporated by reference herein in their entirety.

A fusion protein can be produced, for example, by recombinant expression of a nucleic acid encoding the fusion protein. For example, the fusion protein can be made by fusing a nucleic acid encoding an ECD of ACVR1, ACVR2A and/or ACVR2B to a nucleic acid encoding an Fc domain. The ACVR1, ACVR2A and/or ACVR2B ECD nucleic acid can be fused to the N-terminus of a nucleic acid encoding an Fc domain or can be fused to the C-terminus of a gene encoding an Fc domain. Alternatively, the ECD can be fused at any position in the Fc domain.

The ECD fusion proteins can also include a linker. In the case of an Fc fusion protein, the linker can be positioned between the ACVR1, ACVR2A or ACVR2B ECD and the Fc domain, optionally replacing part or all of the hinge region. The linker can be 1, 2, 3, 4, 5, 6, 7, 8, 9, 10, 15, 20, 30, 50 or more amino acids that are relatively free of secondary structure. A linker can be rich in glycine and proline residues and can, for example, contain repeating sequences of threonine/serine and glycines (e.g., $TG_4$ or $SG_4$ repeats).

Two or more ECD-Fc fusion proteins can be joined together by a linker. In such cases, the linker can be positioned between the ECDs or the linker can be positioned between the Fc domains to join the fusion proteins together. For example, 1, 2, 3, 4 or more ACVR1, ACVR2A and/or ACVR2B Fc fusion proteins can be linked together.

Examples of ACVR2A and/or ACVR2B ECD fusion proteins have been described, such as those disclosed in U.S. Pat. Nos. 7,842,633; 7,960,343; and 7,709,605, each of which is incorporated by reference herein in their entirety.

One example of an ACVR2A antagonist is known as Sotatercept (also called ACE-011). Sotatercept contains the ECD of ACVR2A fused to a human IgG1 Fc domain and is described in detail in Carrancio et al., (2014) *British J Haematology.* 165(6):870-872, which is incorporated by reference herein in its entirety.

One example of an ACVR2B antagonist is known as ACE-031. ACE-031 contains the ECD of ACVR2B fused to a human IgG1 Fc domain and is described in detail in Sako et al., (2010) *J. Biol. Chem.* 285(27):21037-21048, which is incorporated by reference herein in its entirety.

Examples of ACVR1 ECD fusion proteins are known, such as those disclosed in Berasi, et al., (2011) *Growth Factors,* 29(4):128-139; which is incorporated by reference herein in its entirety.

C. Hybrid ECD Fusion Proteins

Hybrid or multispecific ECD fusion protein antagonists are also provided. Hybrid ECD fusion proteins can comprise a combination of two or more ACVR1, ACVR2A and/or ACVR2B ECDs. For example, the fusion proteins can comprise 1, 2, 3, 4 or more molecules of an ACVR1, ACVR2A and/or ACVR2B ECD. In one embodiment, the antagonist comprises an ACVR2A ECD linked to an ACVR2B ECD. In a further embodiment, the antagonist further comprises an Fc domain.

In one embodiment, a fusion protein can comprise one or more molecules of an ACVR2A ECD and one or more molecules of an ACVR2B ECD. In another embodiment, a fusion protein can comprise one or more molecules of an ACVR1 ECD and one or more molecules of an ACVR2A ECD. In another embodiment, a fusion protein can comprise one or more molecules of an ACVR1 ECD and one or more molecules of an ACVR2B ECD.

In one embodiment, a fusion protein comprises one or more ACVR2A ECD-Fc fusion proteins and one or more ACVR2B ECD-Fc fusion proteins which are complexed together. In another embodiment, a fusion protein comprises one or more ACVR1 ECD-Fc fusion proteins and one or more ACVR2A ECD-Fc fusion proteins which are complexed together. In another embodiment, a fusion protein comprises one or more ACVR1 ECD-Fc fusion proteins and one or more ACVR2B ECD-Fc fusion proteins which are complexed together. In such cases, the fusion proteins can be joined together via their Fc domains, for example, by at least one disulfide linkage or by a linker sequence. Alternatively, the ECD portions of the fusion protein can be joined together by a linker sequence.

In one embodiment, the antagonist comprises an ACVR2A ECD fused to a first Fc domain and an ACVR2B ECD fused to a second Fc domain. In such cases, the Fc domains can be complexed with one another. In another embodiment, the antagonist comprises a linker between the ACVR2A and ACVR2B ECDs, each fused to an Fc domain.

The fusion proteins can be constructed to generate ACVR1, ACVR2A, and/or ACVR2B antagonists in a tandem format. In one embodiment, a fusion protein comprises two or more ECDs from ACVR1, ACVR2A and/or ACVR2B in tandem followed by an Fc domain. In some cases the ECDs arranged in tandem are separated by a linker sequence. Such a tandem fusion protein can comprise 1, 2, 3, 4 or more ACVR1, ACVR2A and/or ACVR2B ECDs.

D. Antibody Antagonists

An ACVR1, ACVR2A or ACVR2B antagonist includes antibodies against (in other words specifically binding to) any of these receptors, preferably antibodies having an epitope within the extracellular domain. Specific binding of an antibody or fusion protein to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Methods for preparing antibodies are known to the art. See, for example, Kohler & Milstein (1975) *Nature* 256:495-497; and Harlow & Lane (1988) *Antibodies: a Laboratory Manual*, Cold Spring Harbor Lab., Cold Spring Harbor, N.Y.

Any antibody that inhibits or reduces the activity of ACVR1, ACVR2A and/or ACVR2B (e.g., an antagonist antibody) can be used. Such ACVR2A and ACVR2B antibodies include, for example, those antibodies disclosed in U.S. Pat. Nos. 8,486,403, 8,128,933, WO2009/137075, and Lach-Trifilieff, et al. (2014) *Mol. Cell Biol.* 34(4):606-618, each of which is incorporated by reference herein in their entirety. Humanized, chimeric and veneered forms of any of these antibodies are included as are antibodies competing for binding therewith.

In one embodiment, the antibody is an anti-ACVR2A antibody. In another embodiment, the antibody is an anti-ACVR2B antibody. In other embodiments, the antibody can be a bispecific antibody against both ACVR2A and ACVR2B. In another embodiment, the antibody is an anti-ACVR1 antibody. In other embodiments, the antibody can be a bispecific antibody against both ACVR1 and ACVR2A or against both ACVR1 and ACVR2B.

The term "antibody" covers intact antibodies with two pairs of heavy and light chains, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

"Antibody fragments" comprise a portion of an intact antibody, preferably the antigen-binding or variable region of the intact antibody. Examples of antibody fragments include Fab, F(ab')2, and Fv fragments; diabodies; linear antibodies (Zapata et al. (1995) *Protein Eng.* 10:1057-1062); single-chain antibody molecules; and multispecific antibodies formed from antibody fragments.

The antibody can be monoclonal or polyclonal. A "monoclonal antibody" is an antibody obtained from a population of substantially homogeneous antibodies, that is, the individual antibodies comprising the population are identical except for possible naturally occurring mutations that can be present in minor amounts. Monoclonal antibodies are often highly specific, being directed against a single antigenic site. Furthermore, in contrast to conventional (polyclonal) antibody preparations that typically include different antibodies directed against different determinants (epitopes), each monoclonal antibody is typically directed against a single determinant on the antigen. The modifier "monoclonal" indicates the character of the antibody as being obtained from a substantially homogeneous population of antibodies, such as those produced by a clonal population of B-cells, and does not require production of the antibody by any particular method.

Monoclonal antibodies to be used in accordance with the methods provided herein can be made by the hybridoma method first described by Kohler et al. (1975) *Nature* 256:495, or a modification thereof. Typically, an animal, such as a mouse, is immunized with a solution containing an antigen (e.g., an ACVR1, ACVR2A and/or ACVR2B polypeptide, or Activin A particularly the extracellular domain (in receptors) or a portion thereof).

Immunization can be performed by mixing or emulsifying the antigen-containing solution in saline, preferably in an adjuvant such as Freund's complete adjuvant, and injecting the mixture or emulsion parenterally. After immunization of the animal, the spleen (and optionally, several large lymph nodes) are removed and dissociated into single cells. The spleen cells can be screened by applying a cell suspension to a plate or well coated with the antigen of interest. The B-cells expressing membrane bound immunoglobulin specific for the antigen bind to the plate and are not rinsed away. Resulting B-cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Alternatively, the monoclonal antibodies can be made by recombinant DNA methods (see, e.g., U.S. Pat. No. 4,816, 567). The monoclonal antibodies can also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

"Antibodies" include chimeric, veneered, humanized and human monoclonal antibodies against any of ACVR1, ACVR2A, ACVR2B and Activin A as defined above.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The present monoclonal antibodies or Fc fusion proteins can be any of the various antibody classes. In one embodiment, the monoclonal antibody is an IgG class antibody. In other embodiments, the monoclonal antibody can be of the IgM, IgE, IgD, or IgA class. In specific embodiments, the antibody is an isotype of IgG, such as, IgG1, IgG2, IgG3 or IgG4, particularly human IgG1, IgG2, IgG3 or IgG4.

One or several amino acids at the amino or carboxy terminus of the light and/or heavy chain, such as a C-terminal lysine of the heavy chain, can be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution at any of positions 234, 235, 236 and/or 237 reduces affinity for Fcγ receptors, particularly FcγRI receptor (see, e.g., U.S. Pat. No. 6,624,821). Optionally, positions 234, 236 and/or 237 in human IgG2 are substituted with alanine and position 235 with glutamine. (See, e.g., U.S. Pat. No. 5,624,821). Effector functions can also be reduced by substitution of EFLG at positions 232-236 with PVA (see WO14/121087). Optionally, S at position 428 can be replaced by P, particularly in human IgG4 to reduce exchange between endogenous and exogenous immunoglobulins. Other variations can add or remove sites of post-translational modification, such as N-linked glycosylation at N-X-S/T motifs. Variations can also include introduction of knobs (i.e., replacement of one or more amino acids with larger amino acids) or holes (i.e., replacement of one or more amino acids with smaller amino acids) to promote formation of heterodimers between different heavy chains for production of bispecific antibodies. Exemplary substitutions to form a knob and hole pair are T336Y and Y407T, respectively (Ridgeway et al., Protein Engineering vol. 9 no. 7 pp. 617-621, 1996). Variations can also include mutations that reduce protein A interaction (e.g., H435R and Y436F) in the EU numbering system. Bispecific antibodies in which one heavy chain has such a variation, and another does not, can be separated from their parental antibodies by protein-A affinity chromatography.

Antibodies can also include antibodies specifically binding to Activin A. Such antibodies can specifically bind to any or all of the beta A beta A, beta A beta B, beta A beta C and beta A beta E forms of Activin A. Some antibodies specifically bind to only one of these forms (i.e., beta A beta A, beta A beta B, beta A beta C or beta A beta E). Specificity for the beta A beta B, beta A beta C and beta A beta E forms can be conferred by an epitope within the beta B, beta C or beta E subunit, respectively, or for an epitope to which both components of the heterodimer contribute. Specificity for beta A beta can be conferred by an epitope contributed by both molecules within the homodimer (e.g., at the interface of subunits). Some antibodies specifically bind to all of these forms of Activin A, in which case the epitope is typically on the beta A subunit. Antibodies typically have epitopes within the mature polypeptide component of the precursor proteins. Some antibodies specifically bind to any or all forms of Activin A without binding to human inhibin, which exists in the form of alpha (Swiss Prot P05111) beta A or alpha beta B heterodimers. Some antibodies specifically bind to any or all forms of Activin A and bind to either or both forms of human inhibin. Although it is believed that such antibodies inhibit signal transduction of Activin A through one or more of its counterreceptors, ACVR2A and/or ACVR2B and/or BMPR2, an understanding of mechanism is not required for use of such antibodies in methods of treating FOP.

A substantial number of antibodies against Activin A have been reported. For example, US2015/0037339 discloses human antibodies designated H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10447P2, H4H10448P2, H4H10452P2. U.S. Pat. No. 8,309,082 discloses human antibodies A1-A14. Mouse antibodies against Activin A are available from several commercial suppliers, such as MAB3381 from R&D Systems or 9H16 from Novus Biologicals or MM0074-7L18 (ab89307) AbCam.

Preferred antibodies have an affinity for Activin A (measured at 25° C. as in Example 3 of US2015/0037339) of at least $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. Some antibodies have an affinity within a range of $10^9$-$10^{12}$ $M^{-1}$. Preferred antibodies inhibit signal transduction of Activin A with an IC50 of less than 4 nM, and preferably less than 400 pM or 40 pM. Some antibodies inhibit signal transduction with and IC50 in a range of 4 nM to 10 pM or 3.5 nM to 35 pM.

Signal transduction inhibition can be measured as in Example 6 of US20150037339, which is summarized as follows. A human A204 rhabdomyosarcoma cell line is transfected with a Smad 2/3-luciferase reporter plasmid to produce the A204/CAGAx12-Luc cell line. A204/CAGAx12-Luc cells were maintained in McCoy's 5A supplemented with 10% fetal bovine serum, penicillin/streptomycin/glutamine and 250 µg/mL of G418. For the bioassay, A204/CAGAx12-Luc cells were seeded onto 96-well assay plates at 10,000 cells/well in low serum media, 0.5% FBS and OPTIMEM, and incubated at 37° C. and 5% $CO_2$ overnight. Activin A is serially diluted at 1:3 from 100 to 0.002 nM and added to cells starting along with a control containing no Activin. Antibodies are serially diluted at 1:3 starting from 100 to 0.002 nM, 1000 to 0.02 nM, or 300 to 0.005 nM including control samples containing either an appropriate isotype control antibody or no antibody and added to cells with a constant concentration of 100 pM Activin A.

Some antibodies inhibit binding of Activin A to ACVR2A and/or ACVR2B and/or BMPR2 by at least 1%, 5%, 10%, 20%, 30%, 40%, 50%, 60%, 70%, 80%, 90%, 95%, 99%, as measured when the receptor is expressed from a cell or the extracellular domain is fused with an Fc domain as a fusion protein, and the fusion protein is immobilized to support (e.g., a Biacore sensor chip). In such measurements, the antibody and Activin A should be present in equimolar amounts and the receptor or extracellular domain in excess.

Some antibodies bind to an epitope within residues 321-343 or 391-421 of full-length Activin A, which correspond to C11-S33 and C81-E111 of the mature protein.

An exemplary antibody used in the present examples is designated H4H10446P in US2015037339. Its heavy chain variable region and heavy chain CDR1, CDR2 and CDR3 having the amino acid sequences of SEQ ID NOs:162, 164, 166 and 168, respectively, of US2015/0037339 (present SEQ ID NOs:1-4, respectively). Its light chain variable region and light chain CDRs, CDRL1, CDRL2 and CDRL3 having the amino acid sequences of SEQ ID NO:146, 148, 150 and 152, respectively, of US2015/0037339 (present SEQ ID NOs:5-8, respectively). H4H10446P inhibits Activin A mediated signaling through ACVR2A and/or ACVR2B, but does not inhibit strongly, if at all, Activin A binding to ACVR2A or ACVR2B. Other antibodies competing with H4H10446P for binding to human Activin A or binding to the same epitope on human Activin A as H4H10446P are included and sharing its inhibition of signaling are also included.

Another exemplary antibody for use in the present methods is designated H4H10430P in US2015037339. Its heavy chain variable region and heavy chain CDRs CDRH1, CDRH2 and CDRH3 having the amino acid sequences of SEQ ID NOs:66, 68, 70 and 72, respectively, in US2015/0037339 (present SEQ ID NOs:9-12, respectively). Its light chain variable region and light chain CDRs, CDRL1, CDRL2 and CDRL3 having the amino acid sequences of SEQ ID NOs:74, 76, 78 and 80, respectively, in US2015/0037339 (present SEQ ID NOs:13-16, respectively). This antibody inhibits binding of Activin A to ACVRV2A and/or ACVR2B and inhibits signal transduction through one or both of these receptors. Other antibodies competing with H4H10430P for binding to Activin A or binding to the same epitope on Activin A as H4H10430P and sharing its property of inhibiting Activin A binding to and signal transduction through ACVR2A and ACVR2B are also included.

Another exemplary antibody for use in the present methods is the antibodies designated A1 in U.S. Pat. No. 8,309,082, which is characterized by light and heavy chain variable regions having the sequences SEQ ID NOs:9 and 10 in U.S. Pat. No. 8,309,082 (present SEQ ID NOs:17 and 18, respectively). Its light chain CDRs, CDRL1, CDRL2 and CDRL3 having the sequences SEQ ID NO:11, 12, and 13, respectively, in U.S. Pat. No. 8,309,082 (present SEQ ID NOs:19-21, respectively), and its heavy chain CDRs, CDRH1, CDRH2 and CDRH3 having the sequences SEQ ID NOs: 62, 63 and 64, respectively, in U.S. Pat. No. 8,309,082 (present SEQ ID NOs:22-24, respectively). Other antibodies competing with A1 for binding to Activin A or binding to the same epitope on Activin A as A1 and sharing its property of inhibiting Activin A binding to and transducing a signal through ACVR2A and/or ACVR2B are also included.

Other antibodies can be obtained by mutagenesis of cDNA encoding the heavy and light chains of any of the above-mentioned antibodies. Monoclonal antibodies that are at least 90%, 95% or 99% identical to any of the above-mentioned antibodies in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least 1, 2, 3, 4, 5 and preferably all six CDR(s) that are 90%, 95%, 99% or 100% identical to corresponding CDRs of any of the exemplified antibodies are also included. CDRs are preferably as defined by Kabat, but can be defined by any conventional alternative definition, such as Chothia, composite Kabat-Chothia, the contact definition or AbM definition (see world wide web bioinf.org.uk/abs).

E. Small Molecule Antagonists

Antagonists of ACVR1, ACVR2A and ACVR2B can also be small molecule antagonists. Such small molecule antagonists can inhibit an activity of ACVR1, ACVR2A, ACVR2B or Activin A. Small molecule antagonists of ACVR1 include, for example, LDN-212854 described in Mohedas et al., (2013) *ACS Chem. Biol.* 8:1291-1302, which is incorporated by reference herein in its entirety.

IV. Screening Assays

The activity of the various ACVR1, ACVR2A and/or ACVR2B antagonists and variants or fragments thereof provided herein can be screened in a variety of assays. For example, ACVR1, ACVR2A and/or ACVR2B antagonists and variants thereof can be screened for their ability to bind to ligands or bind to ACVR1, ACVR2A or ACVR2B receptors, for their ability to inhibit binding of a ligand to an ACVR1 and/or ACVR2 polypeptide, and/or for their ability to inhibit activity of the ACVR1 or ACVR2 receptors.

The activity of an ACVR1 or an ACVR2 antagonist or variants or fragments thereof can be tested in vitro or in cell based assays. In vitro binding assays and assays to measure inhibition of receptor activity are well known. Various assays to measure the activity of an ACVR1, ACVR2A or ACVR2B antagonist are described in detail, for example, in U.S. Pat. No. 7,842,663 which is incorporated by reference herein in its entirety.

The ability of the antagonist to modulate complex formation between the ACVR1 or ACVR2 polypeptide and its binding protein can be detected by a variety of techniques. For instance, modulation of the formation of complexes can be quantitated using, for example, detectably labeled proteins such as radiolabeled ($^{32}P$, $^{35}S$, $^{14}C$ or $^{3}H$), fluorescently labeled (e.g., FITC), or enzymatically labeled ACVR1 or ACVR2 polypeptide or its binding protein, by immunoassay, or by chromatographic detection.

The ability of the ACVR1 or ACVR2 antagonist to inhibit ACVR1 or ACVR2 receptor-mediated signaling can be monitored. For example, the effects of downstream signaling such as Smad activation can be monitored using a Smad-responsive reporter gene.

ACVR1 and/or ACVR2 antagonists and variants or fragments thereof can also be screened for activity in an in vivo assay. For example, ACVR1 or ACVR2 antagonists or variants thereof can be screened for their ability to treat FOP in a mouse model of FOP (e.g., ability to decrease ectopic bone formation). Transgenic knock-in mice have been developed that carry a conditional allele encoding Acvr1 [R206H]. These Acvr1$^{[R206H]COIN/+}$ mice are described in U.S. Ser. No. 14/207,320 and PCT/US2014/026582, which are incorporated by reference herein in its entirety. This allele expresses the R206H variant only after activation by Cre recombinase. This allows Cre-dependent activation of Acvr1[R206H] expression at specific tissues and at specific time by using different types of Cre driver lines. In this manner the resulting mice also bypass the perinatal lethality that has been observed with a non-regulated knock-in allele of Acvr1[R206H]. Activation of Acvr1[R206H] expression in young or in adult mice results in ectopic bone formation. For example, Acvr1$^{[R206H]COIN/+}$; Gt(ROSA26)Sor$^{CreERt2/+}$ mice (wherein CreERt2 is a tamoxifen-regulatable recombinase (see Feil et al. (1997) *Biochem Biophys Res Commun.* 237(3):752-7) that has been introduced into the Gt(ROSA26)Sor locus, and hence it is constitutively and globally expressed) develop FOP after exposure to tamoxifen. Briefly, in the absence of tamoxifen, CreERt2 is inactive. Tamoxifen activates expression of Cre which then acts upon the Acvr1$^{[R206H]COIN/+}$ to convert it to Acvr1$^{[R206H]/+}$, thereby converting the genotype of the mice to mirror the genotype of the FOP patients that are ACVR1 [R206H]. The Acvr1$^{[R206H]}$ allele expresses Acvr1[R206H], and that is adequate to drive the development of FOP in the Acvr1$^{[R206H]/+}$; Gt(ROSA26)Sor$^{CreERt2/+}$ mice. This bypasses the embryonic lethality experienced with conventional Acvr1$^{[R206H]}$ knock-in mice, Acvr1$^{tm1Emsh}$ (http://www.informatics.jax.org/allele/key/828153). After tamoxifen treatment, the ACVR1, ACVR2A and/or ACVR2B antagonists or a control can be administered to the Acvr1$^{[R206H]COIN/+}$; Gt(ROSA26)Sor$^{CreERt2/+}$ mice and the animals monitored for ectopic bone formation. See Chakkalakal S A, et al. (20120 An Acvr1 R206H knock-in mouse has fibrodysplasia ossificans progressiva. J Bone Miner Res. 27(8):1746-56. This assay is described in detail in the Examples below.

V. Fibrodysplasia Ossificans Progressiva (FOP)

FOP is a rare heritable disorder in which heterotopic ossification forms histologically and biomechanically 'normal' bone at extraskeletal sites, such as connective tissue. This disorder, although episodic, is cumulative, and results in permanent disability of increasing severity.

FOP's worldwide prevalence is approximately ½,000,000. There is no ethnic, racial, gender, or geographic predilection to FOP. It is not only an extremely disabling disease but also a condition of considerably shortened lifespan.

Characteristics of FOP include, for example, congenital malformations of the great toe, flare-ups characterized by painful soft tissue swellings on the head, neck, and/or back with inflammation and progressive formation of heterotopic bone via endochondral ossification.

FOP can be suspected clinically based on the presence of malformations of the great toe. Diagnostic tests, such as x-rays or bone scan can substantiate great toe abnormalities and confirm the presence of heterotopic ossification. A FOP diagnosis can also be confirmed by genetic testing, for example, by detecting the 617 G-to-A (R206H) mutation in the ACVR1 gene.

It is common for FOP to be misdiagnosed as several other disorders, including other conditions of heterotopic ossification. FOP should be distinguished by a differential diagnosis from disorders including, for example, isolated congenital malformations, lymphedema, soft tissue sarcoma, desmoid tumors, aggressive juvenile fibromatosis, juvenile bunions, isolated brachydactyly, progressive osseous heteroplasia and heterotopic ossification. The presence of great toe congenital malformations and the painful soft-tissue flare-ups can be used to differentiate FOP from other disorders.

Patients with FOP have congenital malformations of the great toe but otherwise appear normal at birth. The flare-ups associated with FOP start during the first decade of life. Flare-ups can be triggered by, for example, soft tissue injury, falls, fatigue, viral infections or intramuscular injections. The result of the flare-ups is a transformation of soft tissue, such as ligaments, skeletal muscle or tendons into heterotopic bone.

There was no previous therapeutic treatment for FOP. FOP was managed by preventative measures, such as improved safety and strategies to minimize injury, avoiding intramuscular injections and taking care when receiving dental care. High dose corticosteroid treatments started within the first 24 hours of a flare-up can help reduce the inflammation and edema associated with flare-ups. Surgical strategies to remove the heterotopic bone are not recommended as it is counterproductive and causes new trauma-induced heterotopic ossification.

FOP is caused by mutations in ACVR1 (also known as ALK2) that appear to destabilize the interaction of the GS domain with an inhibitory molecule, FKBP12 (Groppe, J., et al. 2011, Cells Tissues Organs, 194:291-295). FKBP12 is a negative modulator of ACVR1 and functions to stabilize the receptor in an inactive conformation (Huse, M., et al. 1999, Cell, 96:425-436). See Kaplan, F. S., et al. 2012, Disease Models & Mechanisms, 5:756-762).

An example of a mutation in ACVR1 that is associated with FOP is an Arginine 206 to Histidine (R206H) mutation in the intracellular domain.

A subject at risk of developing FOP includes any subject with the ACVR1 R206H mutation or other mutation associated with FOP, a subject born with malformations of the great toe, or a subject that has a family history of FOP, who has not yet developed symptoms of FOP sufficient for a diagnosis of FOP to be made by art-recognized criteria.

VI. Methods of Treatment

Methods of treating FOP, comprising administering to a subject having FOP an effective regime of an ACVR1, ACVR2A and/or an ACVR2B antagonist are provided herein. In one embodiment, an effective regime of an ACVR2A antagonist and an ACVR2B antagonist is administered. In a further embodiment, the ACVR2A antagonist is an Fc fusion protein and the ACVR2B antagonist is an Fc fusion protein. In another embodiment, FOP is treated by administering an effective regime of an antibody against Activin A.

"Treating" a subject with FOP means administration of an effective regime of an ACVR1, an ACVR2A and/or an ACVR2B antagonist, or an antibody against Activin A, to a subject that has FOP, where the purpose is to cure, heal, alleviate, relieve, alter, remedy, ameliorate, improve, or affect the condition of one or more symptoms of FOP.

A "subject" is any animal (i.e., mammals) such as, humans, primates, rodents, such as mice and rats, agricultural and domesticated animals such as, dogs, cats, cattle, horses, pigs, sheep, and the like, in which one desires to treat FOP. In any of the present methods, the subject can be mammal and preferably human.

An effective regime of an Activin A, ACVR1, ACVR2A and/or an ACVR2B antagonist, or an antibody against Activin A, means a combination of dose, frequency and route of administration of an antagonist which brings a positive response in at least one sign or symptom of FOP. A positive response can include reducing, eliminating, ameliorating, inhibiting worsening of, or delaying at least one sign or symptom of FOP. Signs or symptoms of FOP that can be subject of a positive response include for example, ectopic or heterotopic bone formation, FOP flare-ups, or pain and swelling associated with flare-ups. The regime can be assessed in a single patient by comparing signs and symptoms before and after treatment. A regime is considered effective if at least one sign or symptom gives a positive response following treatment. A regime can alternatively or additionally be assessed by comparing signs and symptoms of population of subjects treated with an antagonist or antagonists of the present invention with a control population of subjects not receiving treatment. The subjects for such comparison can be an animal model, or human subjects in a clinical trial (e.g., phase I, phase II, IIa, IIb, or III). A regime is considered effective if there is a statistically significant positive response between the populations in at least one sign or symptom.

In some methods for treating FOP, the subject does not have and is not at risk of other conditions treatable with antagonists against ACVR1, ACVR2A, and/or ACVR2B, or an antibody against Activin A. For example, the subject can be free of any or all of type II diabetes, muscular dystrophy, amyotrophic lateral sclerosis (ALS) and osteoporosis.

A. Methods of Administration

ACVR1, ACVR2A and/or ACVR2B antagonists, or an antibody against Activin A, are usually administered directly as proteins or small molecules, but in the case of proteins can also be administered as nucleic acid encoding such proteins. Such antagonists can be administered by various methods, such as cellular transfection, gene therapy, direct administration with a delivery vehicle or pharmaceutically acceptable carrier, indirect delivery by providing recombinant cells comprising a nucleic acid encoding an ACVR1, ACVR2A and/or ACVR2B antagonist, or an antibody against Activin A, provided herein.

Various delivery systems can be used to administer the ACVR1, ACVR2A and/or ACVR2B antagonists, or an antibody against Activin A, provided herein, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

Methods of administration can be enteral or parenteral and include intradermal, intramuscular, intraperitoneal, intravenous, subcutaneous, pulmonary, intranasal, intraocular, epidural, and oral routes. The compounds can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the invention into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

The pharmaceutical compositions of the invention can be administered locally to the area in need of treatment; this can be achieved, for example, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In another embodiment, the active agent can be delivered in a controlled release system. In one embodiment, a pump can be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

B. Combination Therapies

The ACVR1, ACVR2A and ACVR2B antagonists, or an antibody against Activin A, provided herein can be administered in combination with one another or other treatments. In one embodiment, the method of treating FOP involves co-administration of an ACVR2A antagonist and an ACVR2B antagonist. In another embodiment, the method of treating FOP involves co-administration of an ACVR1, an ACVR2A and an ACVR2B antagonist. In other embodiments, an ACVR1 antagonist can be co-administered with an ACVR2A and/or an ACVR2B antagonist. The ACVR1, ACVR2A and ACVR2B antagonists can be administered as separate pharmaceutical compositions or can be administered as a single pharmaceutical composition comprising a combination of these agents. The ACVR1, ACVR2A and/or ACVR2B antagonists, or an antibody against Activin A, either alone or in combination, can be administered in conjunction with one or more additional therapeutic compounds. The combination therapy can encompass simultaneous or alternating administration. In addition, the combination can encompass acute or chronic administration.

C. Pharmaceutical Compositions

The present invention also provides pharmaceutical compositions comprising an Activin A, ACVR1, ACVR2A and/or an ACVR2B antagonist, or an antibody against Activin A, provided herein and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In one embodiment, the composition is formulated in accordance with routine procedures as a pharmaceutical composition adapted for intravenous administration to human beings. When necessary, the composition can also include a solubilizing agent and a local anesthetic such as lidocaine to ease pain at the site of the injection. When the composition is to be administered by infusion, it can be dispensed with an infusion bottle containing sterile pharmaceutical grade water or saline. When the composition is administered by injection, an ampoule of sterile water for injection or saline can be provided so that the ingredients can be mixed prior to administration.

The Activin A, ACVR1, ACVR2A and/or an ACVR2B antagonists, or an antibody against Activin A, provided herein can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount and frequency of the Activin A, ACVR1, ACVR2A and/or ACVR2B antagonist, or an antibody against Activin A, administered by a specified route effective in the treatment of FOP (e.g., effective regime) can be determined by standard clinical techniques based on the present description. In addition, in vitro assays can be employed to help identify optimal dosage ranges. The precise dose to be employed in the formulation also depends on the route of administration, and the seriousness of the condition, and should be decided according to the judgment of the practitioner and each subject's circumstances. However, suitable dosage ranges for parenteral administration, preferably intravenous or subcutaneous, are generally about 20-50000 micrograms of active compound per kilogram body weight. For antibodies to Activin A suitable dosage ranges include 1-25 mg/kg, 2-20 mg/kg 5-15 mg/kg, 8-12 mg/kg and 10 mg/kg.

Suitable dosage ranges for intranasal administration are generally about 0.01 pg/kg body weight to 1 mg/kg body weight. Effective doses can be extrapolated from dose-response curves derived from in vitro or animal model test systems.

Frequencies of administration also vary depending on the severity of the condition and half-life of the agent among other factors, but are typically between daily and quarterly, including for example, twice a week, weekly, fortnightly, monthly, bimonthly. Agents can also be administered at irregular intervals responsive to the patient's condition or reduction in serum level of the agent below a threshold among other factors.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise.

EXAMPLES

Example 1: Use of ACVR2A-Fc/ACVR2B-Fc to Suppress Ectopic Bone Formation in a Mouse Model of FOP $Acvr1^{[R206H]COIN/+}$; $Gt(ROSA26)Sor^{CreERt2/+}$ were protected from ectopic bone formation after tamoxifen treatment by ACVR2A-Fc/ACVR2B-Fc treatment.

A mouse model of FOP, referred to as $Acvr1^{[R206H]COIN/+}$; $Gt(ROSA26)Sor^{CreERt2/+}$ were given tamoxifen at 1 mg/mouse dose i.p. for eight days. Eleven mice were treated with 10 mg/kg of ACVR2A-Fc and 10 mg/kg of ACVR2B-Fc twice weekly and ten mice were treated with 10 mg/kg control mFc twice weekly for 6 weeks. Mice were monitored using in vivo μCT at baseline, 2, 4 and 6 weeks post initiation of tamoxifen administration. After 6 weeks, 9 out of 10 mice in the mFc group had developed ectopic bone in at least one location, in contrast only 2 out of 11 mice in the ACVR2A-Fc and ACVR2B-Fc group showed development of ectopic bone and this bone was small in size. These results are shown in FIG. 1.

Example 2: Use of an ACVR1 Kinase Small Molecule Inhibitor to Suppress Ectopic Bone Formation in a Mouse Model of FOP $Acvr1^{[R206H]COIN/+}$; $Gt(ROSA26)Sor^{CreERt2/+}$ were protected from ectopic bone formation after tamoxifen treatment by ACVR1 kinase inhibitor LDN-212854 treatment.

Figure 2:
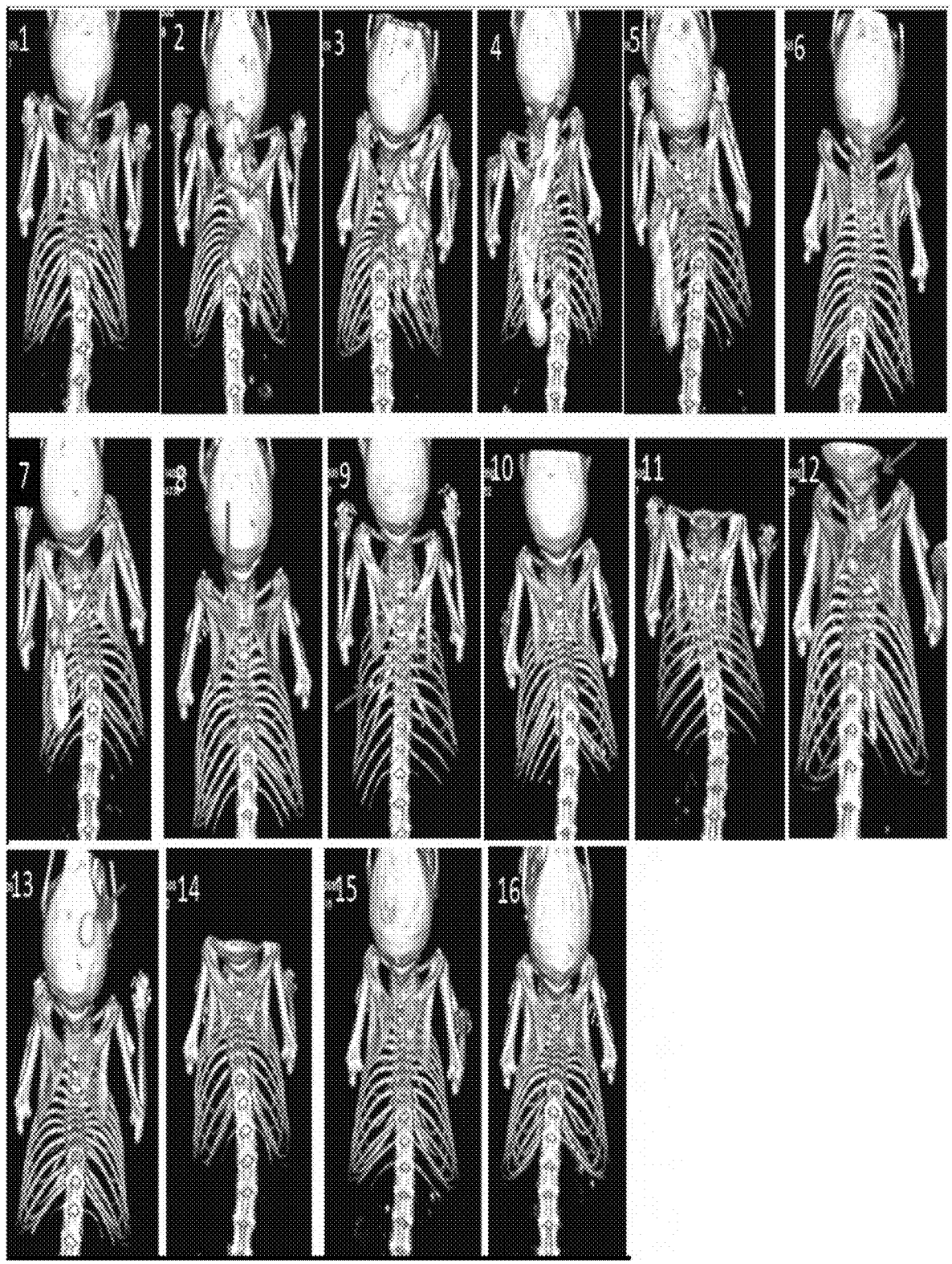
FIG. 2 shows microCT data from mice showing ectopic bone formation 4 weeks post initiation of tamoxifen administration with or without LDN212854 treatment. Numbers 1 to 8 correspond to tamoxifen+vehicle treated mice. Large ectopic bone nodules have formed in mice numbered 1, 2, 3, 4, 5 and 7, and small ectopic bone nodules have formed in mice numbered 6 and 8. Numbers 9-16 correspond to tamoxifen+LDN212854 treated mice. Small ectopic bone nodules have formed in mice numbered 9, 12 and 13. No ectopic bone nodules could be detected in mice numbered 10, 11, 14, 15 or 16.

16 $Acvr1^{[R206H]COIN/+}$; $Gt(ROSA26)Sor^{CreERt2/+}$ mice were given tamoxifen at 1 mg/mouse dose i.p. for eight days. Eight mice were treated with 3 mg/kg of the ACVR1 kinase inhibitor LDN-212854 (Mohedas et al. (2013) *ACS Chem. Biol.* 8:1291-1302) twice daily for 4 weeks. Eight mice were treated with vehicle control twice daily for 4 weeks. Mice were monitored using in vivo μCT at baseline, 2 and 4 weeks post initiation of tamoxifen administration. After 4 weeks 8 out of 8 mice in the vehicle control group showed ectopic bone formation, in 6 of these mice the ectopic bone lesions were large in size. In contrast, in the LDN-212854 treated group, 3 out of 8 mice showed ectopic bone formation, the size of the ectopic bone lesions formed in the 3 mice were small compared to the vehicle control group. These results are shown in FIG. 2.

Figure 3:
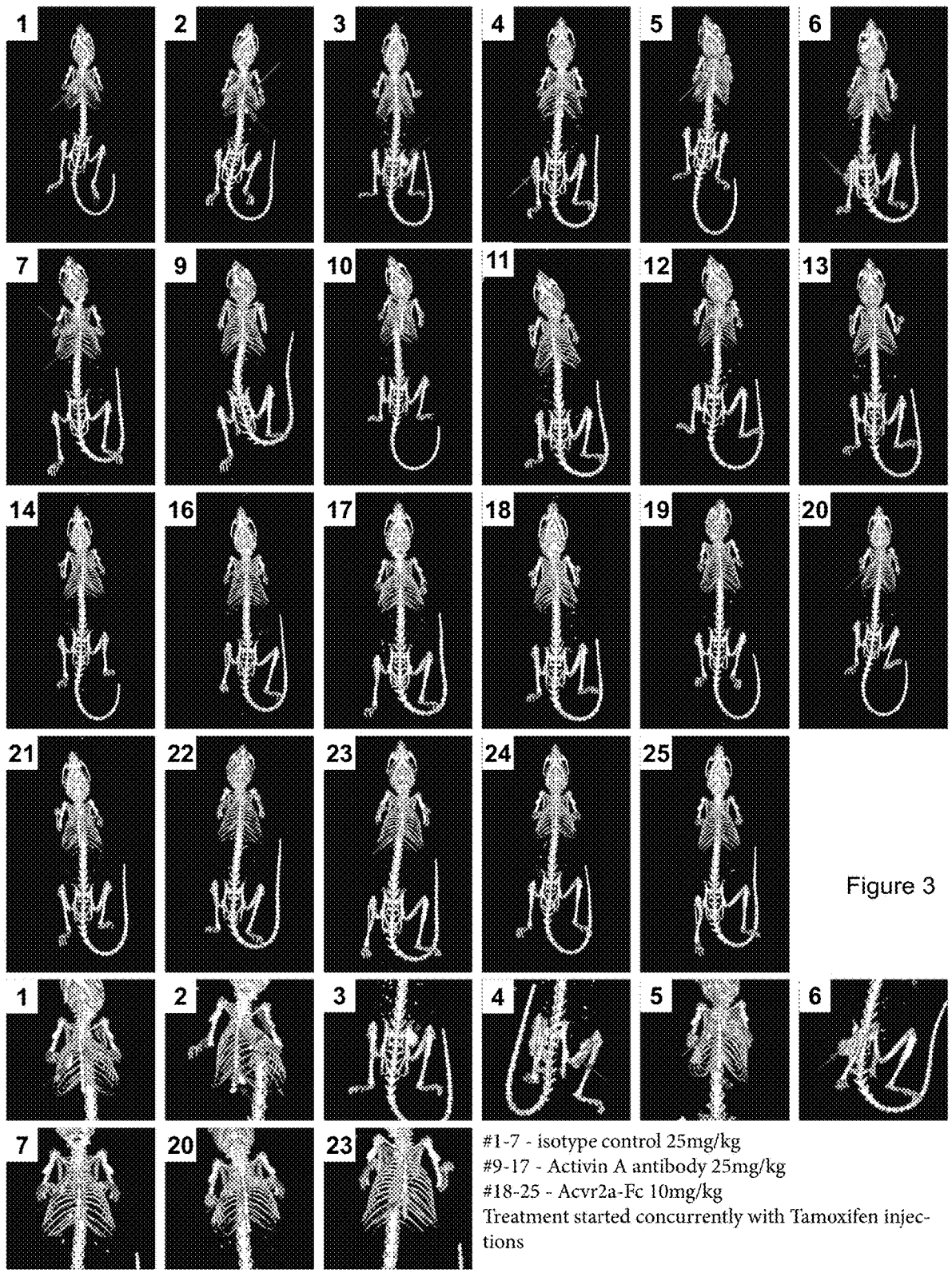
FIG. 3 shows microCT data for mice disposed to ectopic bone formation treated with an antibody against Activin A, an isotype matched irrelevant control antibody, and ACVR2A-Fc. The antibody against Activin A inhibited formation of ectopic bone nodules most effectively.

Example 3: Use of an Antibody Against Activin a to Suppress Ectopic Bone Formation in a Mouse Model of FOP 23 $Acvr1^{[R206H]COIN/+}$; $Gt(ROSA26)^{SorCreERt2/+}$ mice were treated with tamoxifen at 1 mg/mouse dose i.p. for eight days. Seven mice were treated with 25 mg/kg isotype control antibody twice weekly, eight mice were treated with 25 mg/kg of Activin A antibody (H4H10446P) twice weekly, and eight mice were treated with 10 mg/kg of ACVR2a-Fc twice weekly for 3 weeks. Treatments with these agents were started concurrent with initiating tamoxifen treatment. Mice were monitored using in vivo micro computer tomography (μCT) at baseline, 2 and 3 weeks post initiation of tamoxifen administration. FIG. 3 shows that after 3 weeks, all mice in the isotype control antibody group had developed ectopic bone in at least one location, in contrast none of the mice in the Activin A antibody group showed development of ectopic bone at this time. Two mice in the ACVR2a-Fc group developed ectopic bone at 3 weeks.

Example 4

Acvr1[R206H]COIN/+; Gt(ROSA26)SorCreERt2/+ were protected from ectopic bone formation after tamoxifen treatment by both an Activin A and an Acvr2a and b blocking antibody.

Figure 4:
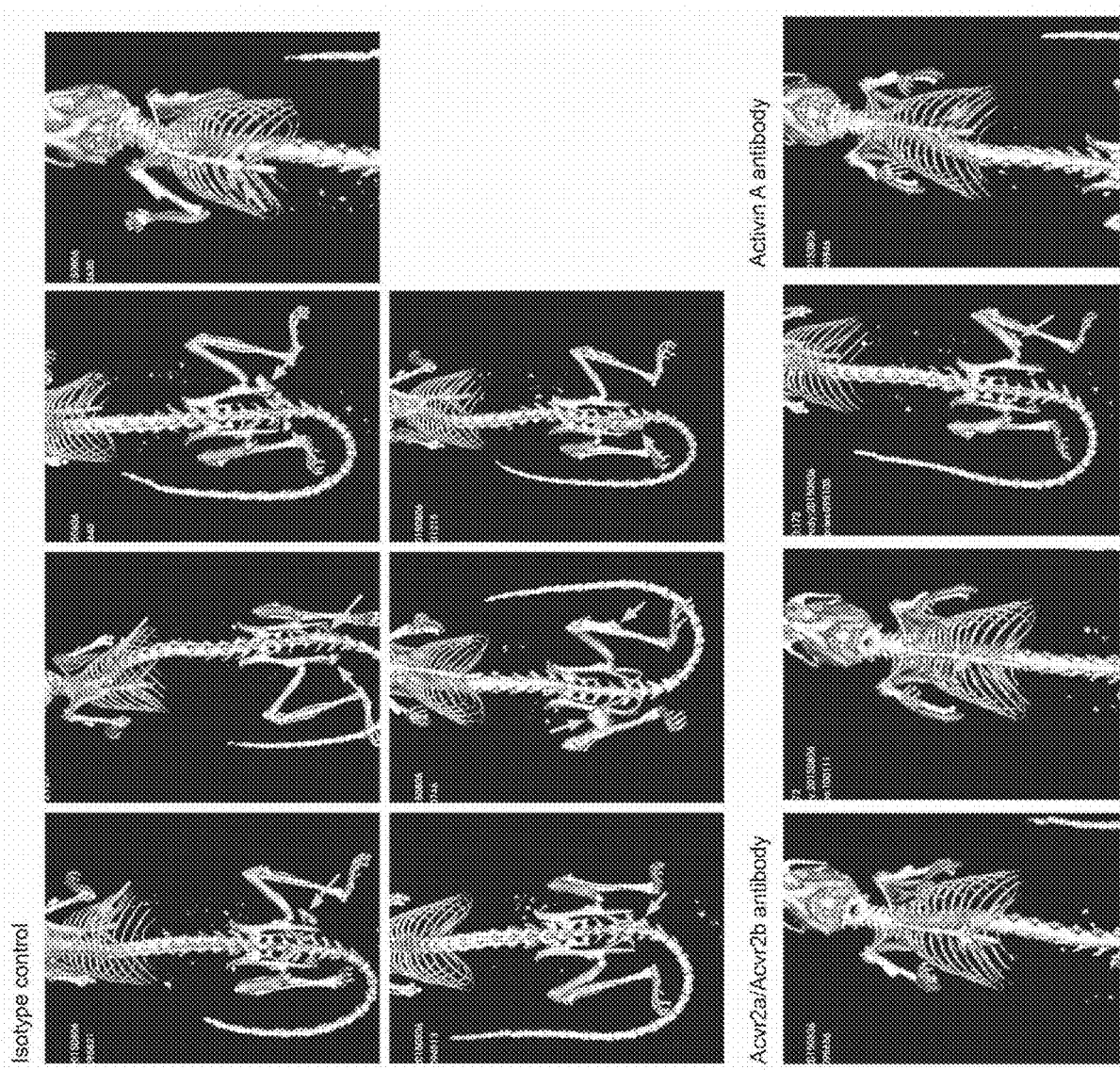
FIG. 4 shows microCT data for mice disposed to ectopic bone formation treated with an antibody against Activin A, an isotype matched irrelevant control antibody, and an antibody against Acvr2a/Acvr2b. The antibody against Activin A and the antibody against Acvr2a/Acvr2b inhibited formation of ectopic bone nodules.

26 Acvr1[R206H]COIN/+; Gt(ROSA26)SorCreERt2/+ mice were given with tamoxifen at a 40 mg/kg dose i.p. for eight days. Eight mice were treated with 10 mg/kg isotype control antibody (REGN1945), nine mice were treated with 10 mg/kg of Activin A antibody (H4H10446P) (REGN2477) and nine mice were treated with 10 mg/kg of an Acvr2a/Acvr2b antibody twice weekly for 6 weeks. Mice were monitored using in vivo μCT at baseline, 2, 3 and 4 weeks post initiation of tamoxifen administration. FIG. 4 shows that after 4 weeks, 7 out of 8 mice in the isotype control antibody group had developed ectopic bone in at least one location, in contrast only one of the mice in the Activin A antibody treated group and three of the mice in the Acvr2a/Acvr2b antibody treated group developed ectopic bone at 4 weeks. The size of the ectopic bone that formed in the antibody treated group was smaller than the isotype control treated group.

Example 5

Acvr1[R206H]COIN/+; Gt(ROSA26)SorCreERt2/+ were protected from ectopic bone formation after tamoxifen treatment by an Activin A blocking antibody.

Figure 5:
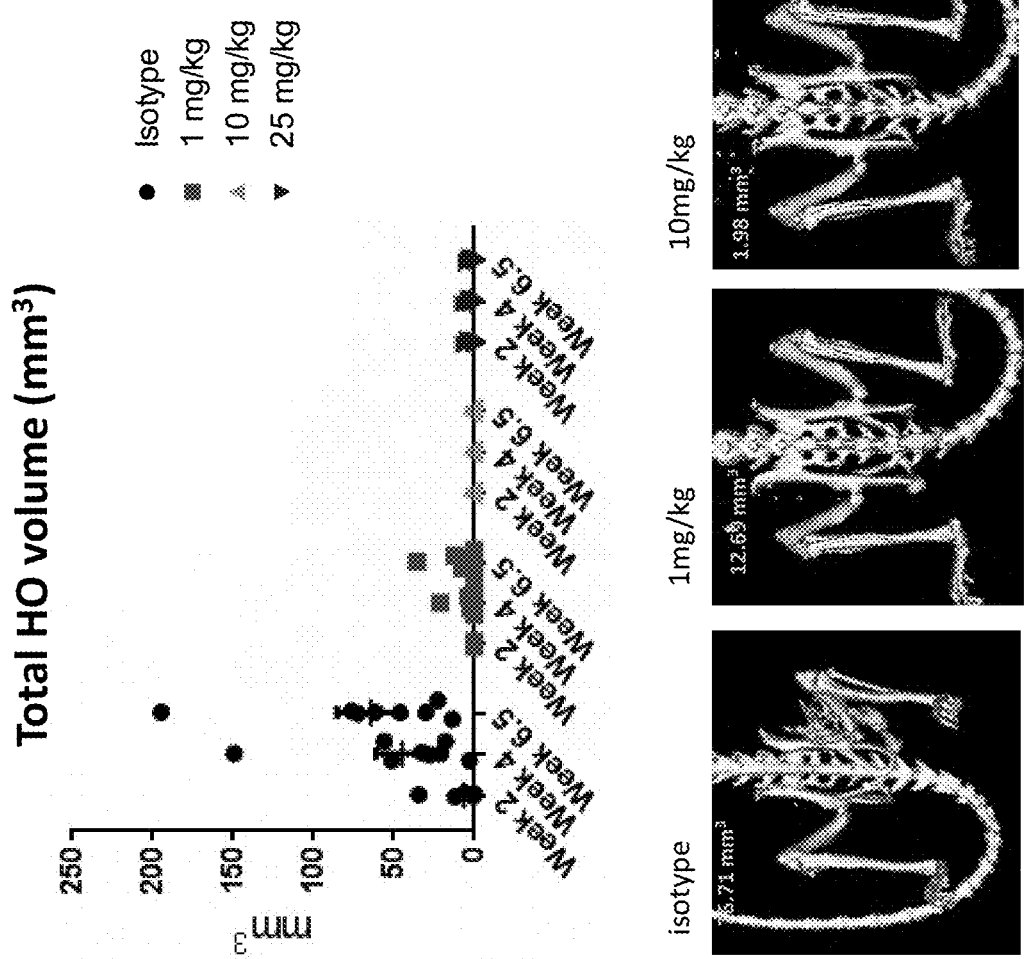
FIG. 5 shows microCT data for mice disposed to ectopic bone formation treated with varying doses of an antibody against Activin A compared with an isotype matched irrelevant control antibody. Dosages between 1 mg/kg and 25 mg/kg were shown to be effective with 10 mg/kg being the most effective dose tested.

35 Acvr1[R206H]COIN/+; Gt(ROSA26)SorCreERt2/+ mice were given with tamoxifen at 40 mg/kg i.p. for eight days. Eight mice were treated with 25 mg/kg isotype control antibody (REGN1945), nine mice were treated with 25 mg/kg of Activin A antibody (H4H10446P) (REGN2477), nine mice were treated with 10 mg/kg of Activin A antibody (REGN2477) and nine mice were treated with 1 mg/kg of Activin A antibody (REGN2477) weekly for 6 weeks. Mice were monitored using in vivo μCT at baseline, 2, 3, 4 and 6.5 weeks post initiation of tamoxifen administration. The volume of ectopic bone in each mouse was calculated from μCT images. FIG. 5 shows after 4 weeks, all mice in the isotype control antibody group had developed ectopic bone in at least one location, whereas only 2 mice each of the Activin A antibody treated groups. At 6.5 weeks the average total volume of ectopic bone in the isotype treated group was 65.4 mm3 compared to 1.87 $mm^3$ in the 25 mg/kg, 0.3 $mm^3$ in the 10 mg/kg and 7.3 $mm^3$ in the 1 mg/kg Activin antibody treated groups.

---

We claim:

1. A method of treating Fibrodysplasia Ossificans Progressiva (FOP), comprising administering to a subject having FOP an effective regime of an antibody against Activin A comprising heavy chain CDR1, CDR2 and CDR3 of SEQ ID NOs: 2-4 respectively, and light chain CDR1, CDR2 and CDR3 of SEQ ID NOs: 6-8 respectively.

2. The method of claim 1, wherein the antibody comprises the heavy chain variable region and the light chain variable region of SEQ ID NOs: 1 and 5 respectively.

3. The method of claim 1 wherein the antibody is an intact antibody.

4. The method of claim 1, wherein the antibody is a human kappa IgG1 antibody.

5. The method of claim 2, wherein the antibody is a human kappa IgG1 antibody.

6. The method of claim 2, wherein the antibody is of human IgG4 isotype.

* * * * *